US007320144B2

(12) United States Patent
Katz et al.

(10) Patent No.: US 7,320,144 B2
(45) Date of Patent: Jan. 22, 2008

(54) PROTECTIVE MASK WITH REMOVABLE LENS

(75) Inventors: Robert Katz, Montréal (CA); Sylvain Duchesne, Bromont (CA)

(73) Assignee: Procaps LP, Saint-Laurent (CA)

( * ) Notice: Subject to any disclaimer, the term of this patent is extended or adjusted under 35 U.S.C. 154(b) by 85 days.

(21) Appl. No.: 11/053,860

(22) Filed: May 9, 2005

(65) Prior Publication Data

US 2006/0176441 A1    Aug. 10, 2006

(30) Foreign Application Priority Data

Feb. 10, 2005   (CA) .................................... 2496868

(51) Int. Cl.
*A42B 3/04* (2006.01)
(52) U.S. Cl. .............................................................. 2/9
(58) Field of Classification Search .................... 2/422, 2/427, 425, 6.7, 6.2, 6.3, 6.4, 429, 9; 292/45, 292/195, 341.17; 24/DIG. 47, DIG. 48
See application file for complete search history.

(56) References Cited

U.S. PATENT DOCUMENTS

| | | | | |
|---|---|---|---|---|
| 3,050,736 | A | * | 8/1962 | Malcom, Jr. .......................... 2/9 |
| 3,783,452 | A | * | 1/1974 | Benson et al. .................... 2/6.4 |
| 4,186,855 | A | * | 2/1980 | Edman et al. ............ 222/321.8 |
| 4,556,995 | A | * | 12/1985 | Yamamoto ....................... 2/439 |
| 5,184,231 | A | * | 2/1993 | Ellis .............................. 359/13 |
| 6,189,156 | B1 | * | 2/2001 | Loiars ........................... 2/424 |
| 6,381,749 | B1 | | 5/2002 | Cyr |
| RE37,816 | E | * | 8/2002 | Kranhouse .................... 351/43 |
| 6,718,561 | B2 | * | 4/2004 | Dondero ......................... 2/436 |
| 6,886,183 | B2 | * | 5/2005 | DeHaan et al. ................. 2/6.7 |
| 7,003,802 | B2 | * | 2/2006 | Broersma ........................... 2/9 |

OTHER PUBLICATIONS

JTUSA,. as found on website www.itusa.com/iframee.asp.
Website www.vforcepaintball.com/.
esportsman.com, as found on website www.esportsman.com/catalog/index.php/cPath/43 45.
Bigfoot Paintball, as found on websites www.proshop.bigfootpaintball.com/index.php?section=masques&soussection=moyendegamme and www.proshop.bigfootpaintball.com/index.php?section=masques&soussection=hautegamme.

* cited by examiner

*Primary Examiner*—Shaun R. Hurley
(74) *Attorney, Agent, or Firm*—Ogilvy Renault LLP

(57) ABSTRACT

A protective mask and method, comprising a face mask having a body shaped so as to generally cover a face of the user person. The body defines an opening opposite the eyes of the user person when the face mask is worn. A removable lens has a lens portion of see-through material covering the opening so as to protect the eyes of the user person while allowing visibility of the user person therethrough, and connector portions at opposed ends of the lens portion. Clamping devices are positioned in the face mask at opposed ends of the opening. The clamping devices each have a clip with a catch pivotally mounted to the face mask so as to be displaceable to a locking position, in which the catch engages with the respective connector portion to releasably secure the removable lens to the face mask.

20 Claims, 4 Drawing Sheets

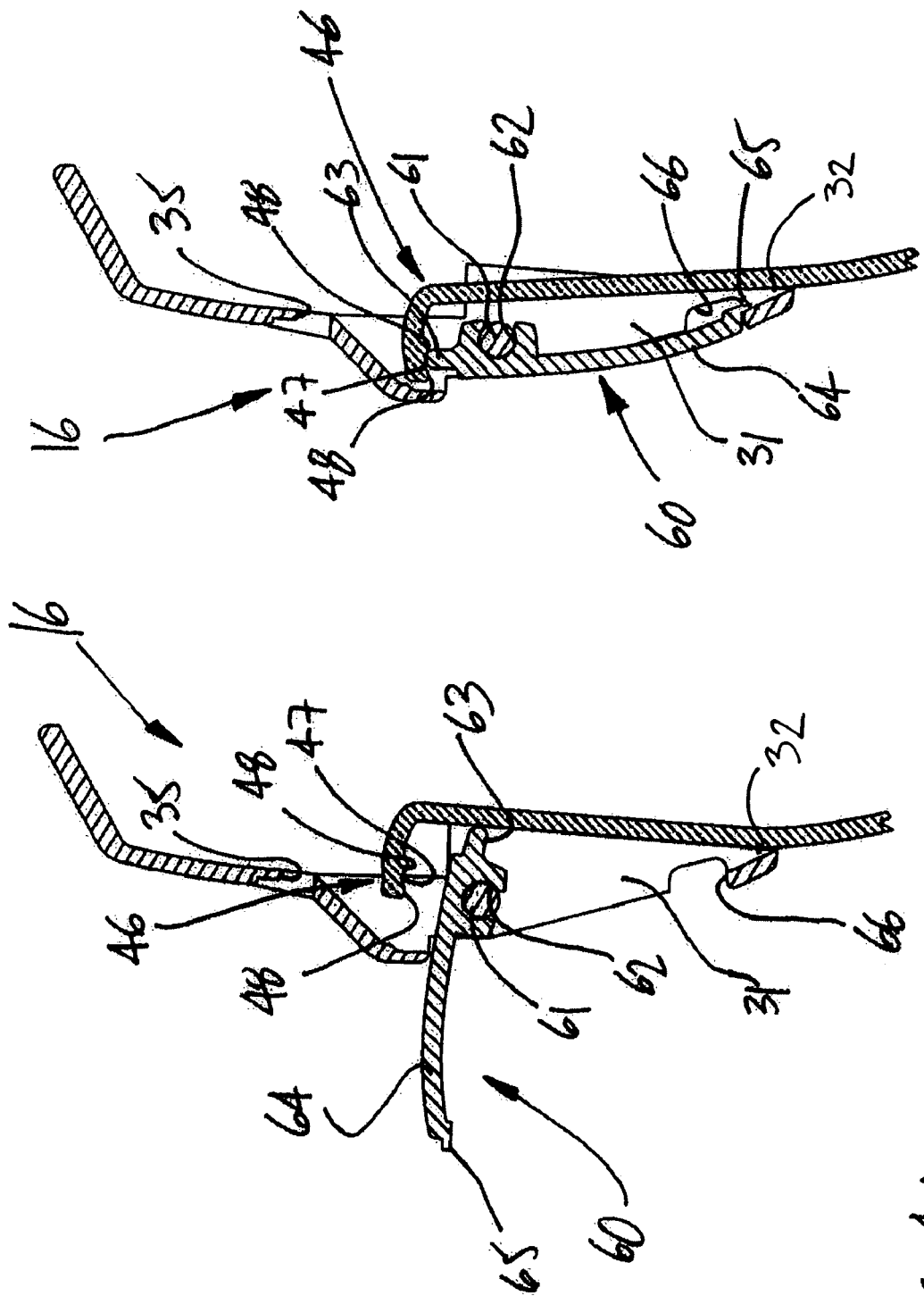

PROTECTIVE MASK WITH REMOVABLE LENS

CROSS-REFERENCE TO RELATED APPLICATION

The present patent application claims priority on Canadian Patent Application No. 2,496,868, filed Feb. 10, 2005, by the present applicants.

TECHNICAL FIELD

The present invention generally relates to protective masks used in physical games and sports, such as paintball games.

BACKGROUND ART

Protective masks are used in physical games in which the head of the player may be subjected to impacts and projectiles. For instance, the game of paintball is a simulation of a war game in which participants eliminate other participants by hitting the latter with paint bullets that will visually display a hit.

Accordingly, in such games, full face masks are worn to protect the face and the eyes of the participants from the projectiles. Such protective masks have see-through lenses, which protect the eyes from projectiles while not impeding the vision of the wearer.

Due to the physical nature of such games, the see-through lens may be damaged by projectiles or through physical contact, or simply dirtied by paint or the like. Therefore, the lens is often removable from the face mask, so as to be replaced or cleaned.

To facilitate removal and installation of see-through lenses from face masks, various connection systems have been developed. For instance, U.S. Pat. No. 6,381,749, issued to Cyr on May 7, 2002, describes an anchor clamp for releasably securing a see-through lens to a face mask. This anchor clamp has a wedge portion that is connected to a strap. This wedge portion is displaceable with respect to the strap so as to reach a position in which the lens is retained to the face mask.

Due to the risks associated with inadvertent disengagement of a lens from the face mask, it is desired to provide protective masks providing secure connections of the lens to the face mask. On the other hand, the lens must be replaceable, and this should ideally be rapidly and simply executed.

SUMMARY OF INVENTION

Therefore, it is a feature of the present invention to provide a novel protective mask having a removable lens.

It is a further feature of the present invention that the connection between the removable lens and an associated face mask be secure, and easy to use.

It is a still further feature of the present invention to provide a novel method for installing a removable lens on a face mask.

Therefore, according to the present invention, there is provided a protective mask, comprising: a face mask adapted to be worn by a user person, the face mask having a body shaped so as to generally cover a face of the user person, the body defining an opening opposite the eyes of the user person when the face mask is worn; a removable lens having a lens portion of see-through material covering the opening so as to protect the eyes of the user person while allowing visibility of the user person therethrough, and connector portions at opposed ends of the lens portion; and clamping devices positioned in the face mask at opposed ends of the opening, the clamping devices each having a clip, each of the clips having a catch and being pivotally mounted to the face mask so as to be displaceable between a locking position, in which the catch engages with the respective connector portion to releasably secure the removable lens to the face mask, and a release position, in which the catch is away from the connector portion, to enable removal of the removable lens from the face mask.

Further in accordance with the present invention there is provided a method for installing a removable lens on a face mask in a protective mask, comprising the steps of: i) providing a face mask having an opening opposite the eyes of the user person when the face mask is worn, a removable lens having a lens portion and connector portions at opposed ends of the lens portion, and clamping devices to secure the removable lens to the face mask; ii) pressuring the removable lens such that connector portions are brought closer to one another; iii) inserting the connector portions into the opening of the face mask; iv) releasing a pressure from the removable lens such that the connector portions bias away from each other; and v) engaging the clamping devices with the connector portions so as to secure the removable lens to the face mask.

BRIEF DESCRIPTION OF DRAWINGS

A preferred embodiment of the present invention will now be described with reference to the accompanying drawings in which:

FIG. 4A is an enlarged cross-sectional view of a clamping device of the protective mask, prior to the removable lens being secured to the face mask; and FIG. 4B is an enlarged cross-sectional view of the clamping device of the protective mask, with the removable lens being secured to the face mask.

DESCRIPTION OF PREFERRED EMBODIMENTS

Figure 1:
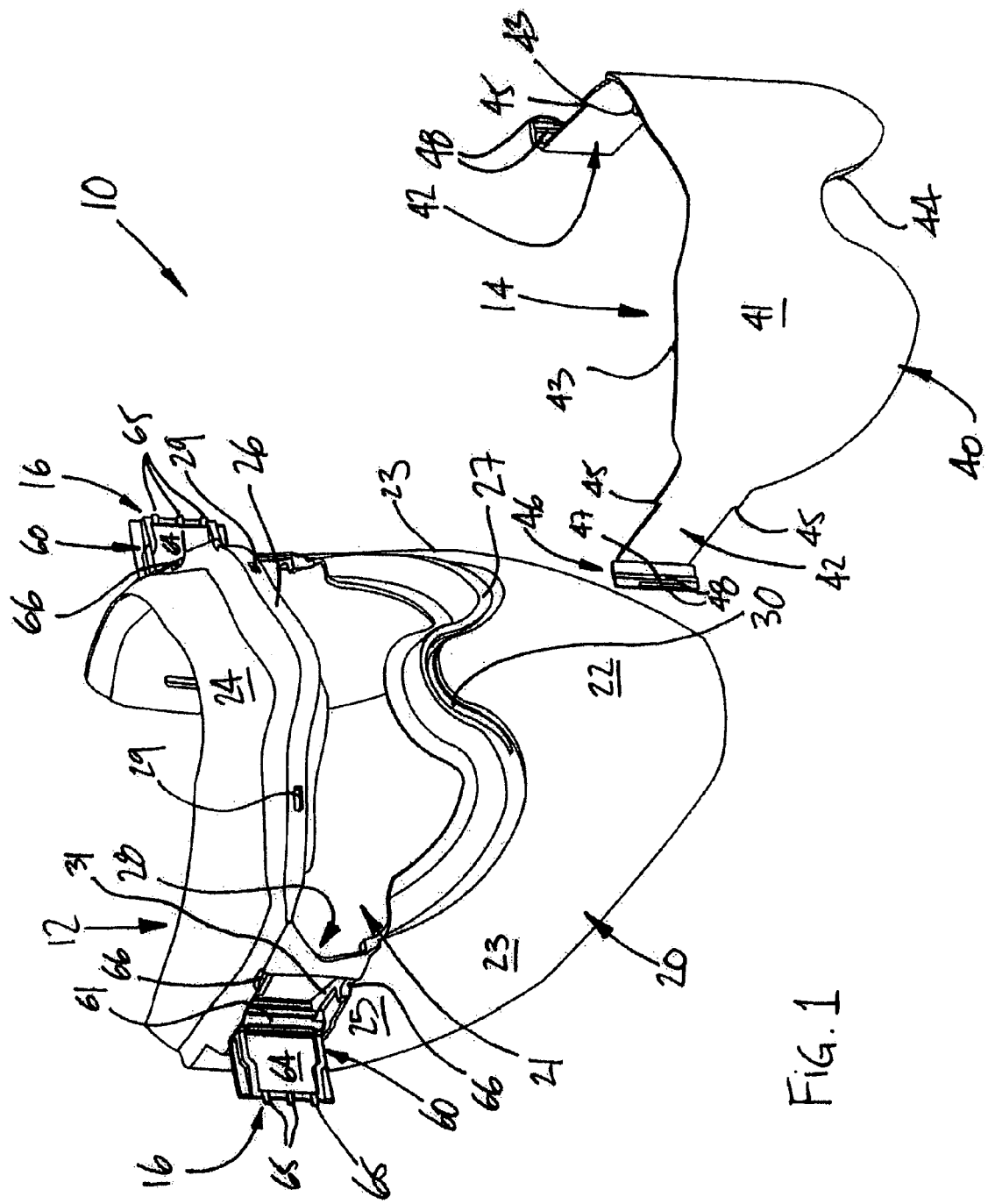
FIG. 1 is an exploded view of a protective mask in accordance with a preferred embodiment of the present invention, with a removable lens being separated from a face mask.

Referring to the drawings, and more particularly to FIG. 1, a protective mask in accordance with a preferred embodiment of the present invention is generally shown at 10. The protective mask 10 has a face mask 12 and a removable lens 14. The removable lens 14 is releasably secured to the face mask 12 by a pair of clamping devices 16, positioned on opposite sides of the face mask 12.

The Face Mask 12

The face mask 12 is generally presented as having a body 20 covering the face of the user person. An opening 21 is defined in the body 20, and the opening 21 is opposite the eyes of the user person when the face mask 12 is worn.

The body 20 covers the front and the sides of the face of the user person, and therefore has a nose/mouth portion 22, cheek portions 23, a brow portion 24 and temple portions 25. The temple portions 25 extend above and beyond the ears of the wearer of the face mask 12. Although not illustrated for simplicity purposes, vent holes are appropriately provided all over the body 20, for the comfort of the user person. It is pointed out that the vent holes are either smaller than the projectiles used in the game (if applicable), or backed up by a mesh lining (or the like) blocking the vent holes. The body 20 typically consists of a molded plastic, but may alternatively be of other materials. For instance, a thermoplastic is well suited material to make up the body 20 of the face mask 12.

The opening 21 in the body 20 is surrounded by an upper flange 26 in the brow portion 24, and a lower flange 27 in the nose/mouth portion 22 and the cheek portions 23. The lower flange 27 defines a sinuous shape. The clamping devices 16 are positioned in the temple portions 25, and are separated from the flanges 26 and 27 by channels 28. Channels 28 are provided in the temple portions 25, and receive therein a portion of the removable lens 14, as will be described hereinafter.

A strap (not shown) is, for instance, used with the face mask 12 to secure the body 20 of the face mask 12 to the head of the user. The strap or like connection means are, for instance, used in combination with strap apertures, one of which is shown at 35 in FIGS. 4A and 4B.

Removable Lens 14

Figure 3:
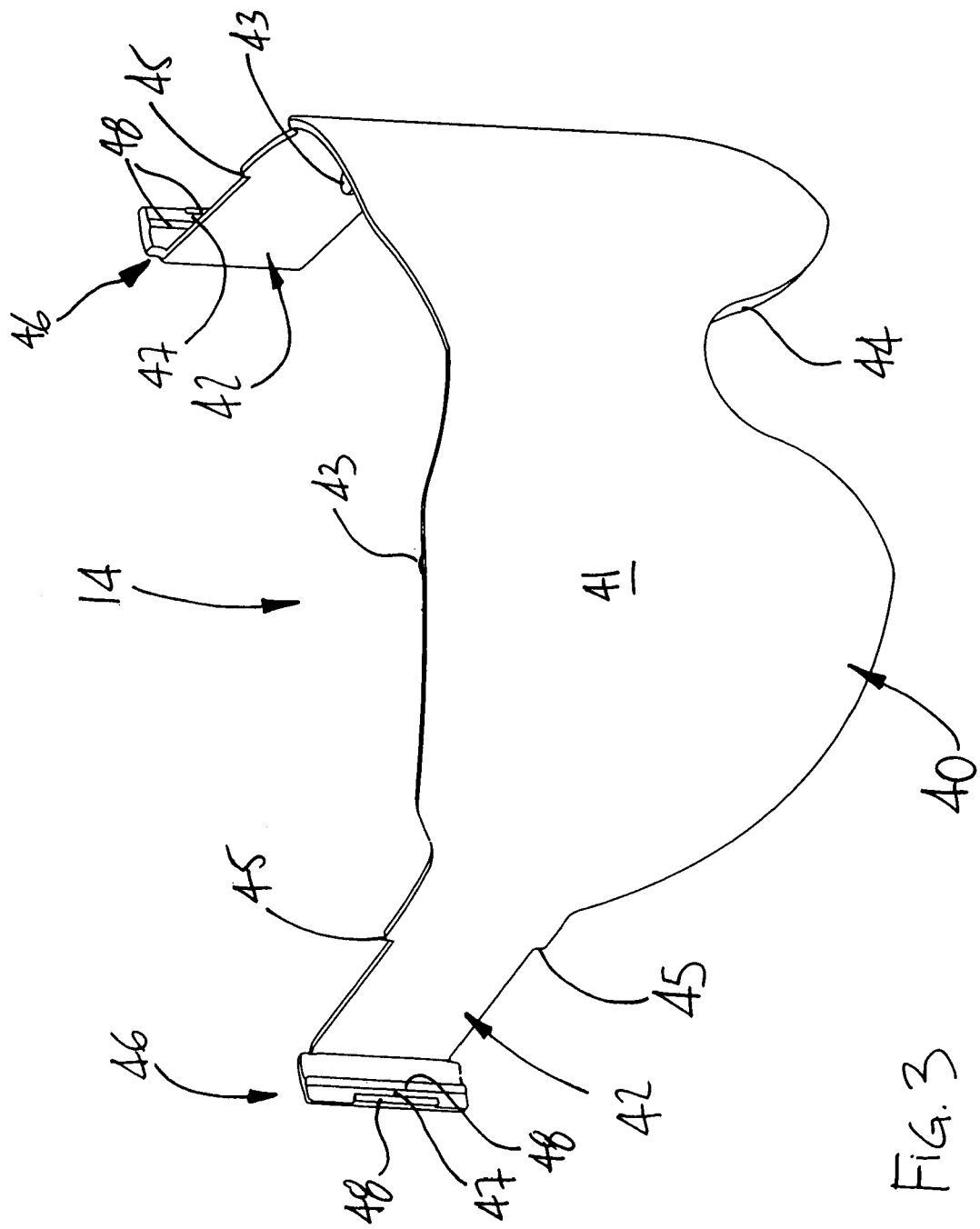
FIG. 3 is a perspective view of the removable lens.

Referring to FIG. 3, the removable lens 14 is shown having a body 40 of see-through material. In an embodiment, the body 40 of the lens 14 is integrally made from polycarbonate, and is flexible. The body 40 has a lens portion 41, and connector tongues 42 at opposed ends of the lens portion 41.

Tabs 43 are provided adjacent to an upper edge of the lens portion 41, for alignment of the removable lens 14 with the face mask 12. A flange 44 is provided at a bottom edge of the lens portion 41, also for alignment of the removable lens 14 with the face mask 12.

The connector tongues 42 each have a pair of abutments 45. The abutments 45 are respectively positioned at an upper and a lower edge of the connector tongues 42.

Connector flanges 46 protrude laterally from the connector tongues 42. As seen concurrently in FIGS. 3, 4A and 4B, the connector flange 46 shown has a concavity 47, defined between vertical ribs 48.

Clamping Devices 16

Figure 2:
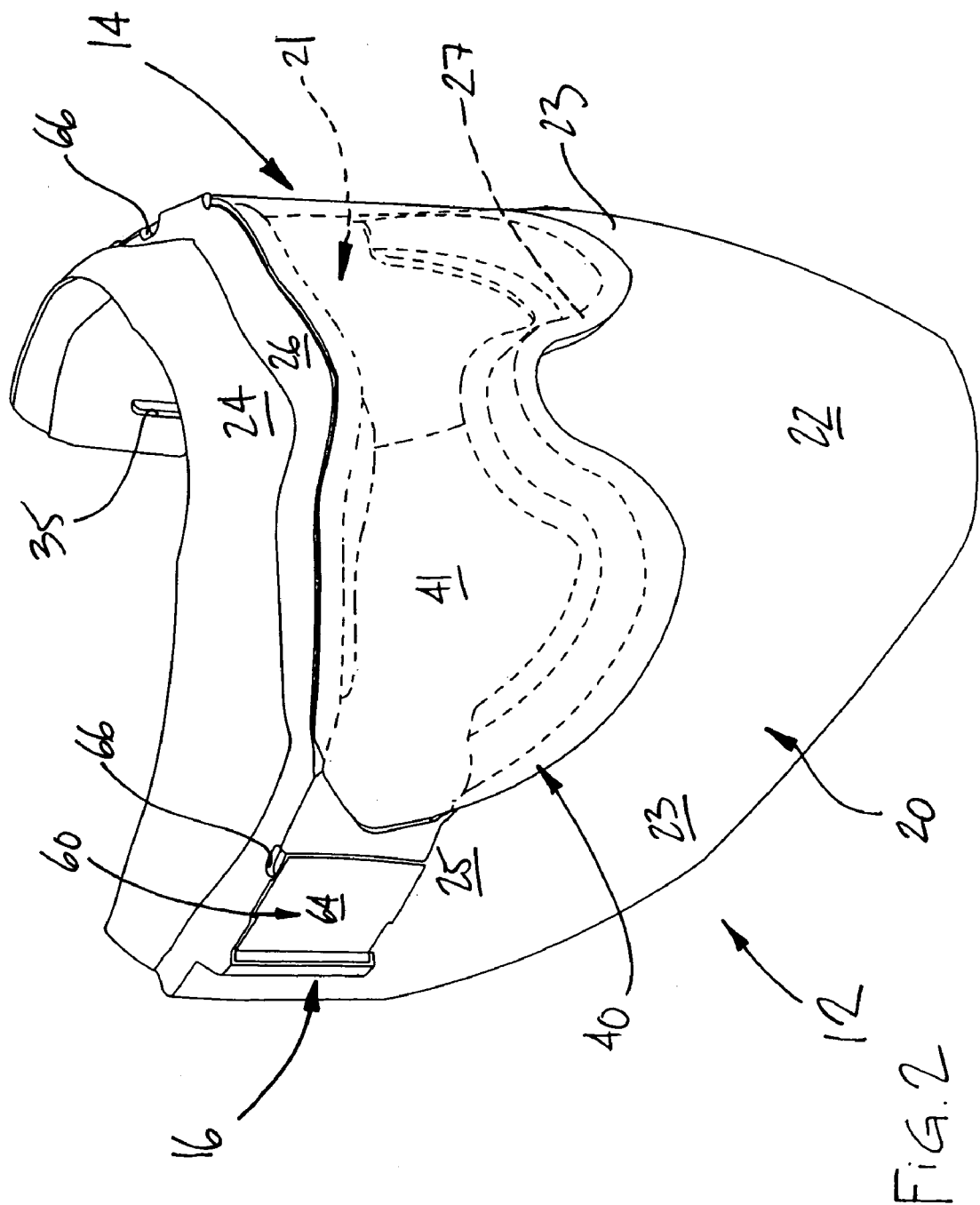
FIG. 2 is a perspective view of the protective mask of the present invention, with the removable lens secured to the face mask.

Referring concurrently to FIGS. 1 and 3, the clamping devices 16 are shown each having a clip 60. In FIGS. 1 and 4A, the clips 60 are in a release position, in which the clips 60 are pivoted away from the face mask 12, so as not to cooperate with the removable lens 14, for connecting/releasing the removable lens 14 to/from the face mask 12. In FIGS. 2 and 4B, the clips 60 are in a locking position, in which the clips 60 cooperate with the removable lens 14 so as to secure the removable lens 14 to the face mask 12.

Referring to FIGS. 4A and 4B, the clip 60 (only one of which is visible) is pivotally secured to post 61. The post 61 is preferably integrally formed into the body 20 of the face mask 12. The clip 60 has a receptacle 62 accommodating the post 61. The receptacle 62 has an open end, and the clip 60 is snap-fitted to the post 61.

The clip 60 has a catch 63 facing toward a rear end of the face mask 12 when the clip 60 is in the locking position. The clip 60 has a major portion 64 extending in an opposite direction to the catch 63. The major portion 64 extends laterally from the face mask 12 in the release position of the clamping device 16, so as to be readily handled by a user person for pivoting the clip 60 to the locking position of FIG. 4B.

Fingers 65 are provided at an end of the major portion 64, so as to snap the clip 60 to the locking position in FIG. 4B, in which the clip 60 is generally coplanar with an adjacent portion of the face mask 12, thereby defining a smooth surface therewith. This generally prevents the clip 60 from accidentally being dislodged from the locking position. Moreover, a snapping noise is caused by the clip 60 reaching its locking position, indicating that the removable lens 14 is secured to the face mask 12. Alternatively, a full edge could be provided instead of the three fingers 65 illustrated in FIG. 1.

Finger apertures 66 are provided in the face mask 12 adjacent to a front edge of the clip 60, both above (FIG. 1) and below the clip 60, to facilitate the grasping of the clip 60 by a user person disengaging the clip 60 from the locking position of FIG. 4B.

Referring to FIGS. 4A and 4B, it is seen that the catch 63 is significantly shorter than the major portion 64 with respect to the post 61. Accordingly, it would take a substantially greater force on the catch 63 to dislodge the clip 60 from its locking position. Moreover, considering that the fingers 65 are snapped to the face mask 12, the clip 60 is generally prevented from inadvertently being dislodged from the locking position, thereby ensuring that the removable lens 14 remains secured to the face mask 12.

Alignment Between Face Mask 12 and Removable Lens 14

Referring to FIG. 2, the removable lens 14 is shown secured to the face mask 12. The removable lens 14 must be aligned in the face mask 12 to ensure that the opening 21 in the face mask 12 is fully covered by the removable lens 14. Accordingly, as is described hereinbelow, means are provided to align the removable lens 14 with the face mask 12.

Referring to FIG. 1, a pair of slots 29 are provided in the upper flange 26, for complementary engagement with the corresponding tabs 43 of the removable lens 14. Similarly, a channel 30 is provided in the lower flange 27, in the nose region, for complementary engagement with the corresponding flange 44 of the removable lens 14. Therefore, the removable lens 14 is aligned with the face mask 12 when positioned thereon, by the cooperation of the tabs 43 and flange 44 with the slots 29 and the channel 30, respectively.

Connection of the Removable Lens 14 to the Face Mask 12

Referring concurrently to FIGS. 1 and 2, the channels 28 (FIG. 1) in the temple portions 25 are sized to receive the connector tongues 42 of the removable lens 14. As it is flexible, the removable lens 14 is slightly bent so as to fit the connector tongues 42 within the channels 28. Once the lens 14 is in position, the lens 14 biases back to its shape. As partially shown in FIGS. 1, 4A and 4B, upper and lower guide edges 31 are provided in the channels 28. The upper and lower guide edges 31 are spaced apart by a distance generally equivalent to the height of the connector tongues 42. Accordingly, the connector tongues 42 are generally prevented from moving in the vertical direction.

Abutments 32 (only one of which is shown at 32 in FIGS. 4A and 4B) are provided in front of the guide edges 31. The abutments 32 cooperate with the abutments 45 (FIGS. 1 and 3) of the removable lens 14, to adjust a horizontal positioning of the connector tongues 42 in the channels 28 of the face mask 12.

Accordingly, by way of these above-described vertical and horizontal positioning configurations, the connector tongues 42 are positioned within the channels 28 in such a way that the connector flanges 46 are adjacent to the catches 63 of the clamping devices 16. More specifically, referring to FIG. 4A, when the removable lens 14 is mounted to the face mask 12 (FIG. 2), the connector flange 46 is positioned rearward of the post 61.

In order to secure the removable lens 14 to the face mask 12, the clip 60 is pivoted from its release position of FIG. 4A, to its locking position of FIG. 4B, in which the catch 63 will be lodged within the concavity 47 of the connector flange 46. In doing so, the catch 63 rides over one of the vertical ribs 48 to reach the concavity 47.

Moreover, referring to FIG. 4B, it is pointed out that the removable lens 14 exerts a pressure on the clips 60 once the clips 60 are in their locking positions of FIG. 4B. The pressure is transmitted to the catch 63 of the clips 60 by the concavity 47 and the vertical ribs 48. Advantageously, a pivot axis of the post 61 is positioned inward of the catch 63 with respect to the respective connector tongues 42. Therefore, the pressure exerted onto the catch 63 by the lens 14 will create an additional force keeping the clip 60 into the locking position of FIG. 4B.

To remove the lens 14 from the face mask 12, the clamping devices 16 are firstly disengaged with the connector tongues 42. The removable lens 14 is pressured such that the connector tongues 42 are brought closer to one another. The connector tongues 42 are then pulled out of the opening of the face mask 12.

It is within the ambit of the present invention to cover any obvious modifications of the embodiments described herein, provided such modifications fall within the scope of the appended claims.

The invention claimed is:

1. A protective mask, comprising:
   a face mask adapted to be worn by a user person, the face mask having a body shaped so as to generally cover a face of the user person, the body defining an opening opposite the eyes of the user person when the face mask is worn;
   a removable lens having a lens portion of see-through material covering the opening so as to protect the eyes of the user person while allowing visibility of the user person therethrough, and connector portions at opposed ends of the lens portion; and
   clamping devices positioned in the face mask at opposed ends of the opening, the clamping devices each having a clip, each of the clips having a front end adjacent to the lens portion, a rear end away from the lens portion, and a catch being positioned at the rear end of the respective clip, the clips each being pivotally mounted to the face mask so as to be displaceable between a locking position, in which the catch engages with the respective connector portion to releasably secure the removable lens to the face mask, and a release position, in which the catch is away from the connector portion, to enable removal of the removable lens from the face mask, wherein at least one finger is provided at the front end of the clip, for snap-fitting engagement of the clips to the face mask when the clips reach the locking position.

2. The protective mask according to claim 1, wherein a pivot axis of each of the clamping devices is substantially closer to the rear end of the clip.

3. The protective mask according to claim 1, wherein a pivot axis of each of the clamping device is positioned inwardly to the protective mask with respect to the catch, such that pressure exerted on the catch by the respective connector portion pressures the clip into the locking position.

4. The protective face mask according to claim 1, wherein the at least one finger is at a front edge of the clip.

5. The protective mask according to claim 1, wherein the face mask has at least one aperture adjacent to the front end of each of the clips, for manually disengaging the clip from the locking position.

6. The protective mask according to claim 1, wherein each of the clips has a generally smooth surface, the smooth surface being generally flush with an adjacent surface of the face mask when the clips are in the locking position.

7. The protective mask according to claim 1, wherein each of the clips has a receptacle releasably secured to a post in the face mask for pivoting of the clips.

8. The protective mask according to claim 1, wherein the connector portions of the removable lens each have a laterally projecting connector flange having a concavity to accommodate the catch of the respective clamping devices in the locking position.

9. The protective mask according to claim 1, wherein the face mask has at least one aperture in the periphery of the opening, for accommodating a complementary protrusion in the lens portion for alignment of the removable lens with the face mask.

10. The protective mask according to claim 9, wherein the at least one aperture is a sinuous channel in a nose-covering portion of the face mask.

11. The protective mask according to claim 1, wherein the face mask defines channels on opposite sides of the opening, for receiving the connector portions of the removable lens, the channels each defining guide edges for guiding the connector portions into position with respect to the clamping devices.

12. The protective mask according to claim 11, wherein the connector portions and the channels are provided with corresponding abutments for aligning the connector portions into position with respect to the clamping devices.

13. A protective mask, comprising:
   a face mask adapted to be worn by a user person, the face mask having a body shaped so as to generally cover a face of the user person, the body defining an opening opposite the eyes of the user person when the face mask is worn;
   a removable lens having a lens portion of see-through material covering the opening so as to protect the eyes of the user person while allowing visibility of the user person therethrough, and connector portions at opposed ends of the lens portion; and
   clamping devices positioned in the face mask at opposed ends of the opening, the clamping devices each having a clip, each of the clips having a catch and being pivotally mounted to the face mask so as to be displaceable between a locking position, in which the catch engages with the respective connector portion to releasably secure the removable lens to the face mask, and a release position, in which the catch is away from the connector portion, to enable removal of the removable lens from the face mask, wherein each of the clips has a receptacle releasably secured to a post in the face mask for pivoting of the clips.

14. The protective mask according to claim 13, wherein each of the clips has a front end adjacent to the lens portion, and a rear end away from the lens portion, the catch being positioned at the rear end of the respective clip.

15. The protective mask according to claim 14, wherein a pivot axis of each of the clamping devices is substantially closer to the rear end of the clip.

16. The protective mask according to claim 14, wherein a pivot axis of each of the clamping device is positioned inwardly to the protective mask with respect to the catch, such that pressure exerted on the catch by the respective connector portion pressures the clip into the locking position.

17. The protective mask according to claim 13, wherein the connector portions of the removable lens each have a laterally projecting connector flange having a concavity to accommodate the catch of the respective clamping devices in the locking position.

18. A protective mask, comprising:
- a face mask adapted to be worn by a user person, the face mask having a body shaped so as to generally cover a face of the user person, the body defining an opening opposite the eyes of the user person when the face mask is worn;
- a removable lens having a lens portion of see-through material covering the opening so as to protect the eyes of the user person while allowing visibility of the user person therethrough, and connector portions at opposed ends of the lens portion, wherein the connector portions of the removable lens each have a laterally projecting connector flange having a concavity; and
- clamping devices positioned in the face mask at opposed ends of the opening, the clamping devices each having a clip, each of the clips having a catch and being pivotally mounted to the face mask so as to be displaceable between a locking position, in which the catch is accommodated in the concavity of the respective connector portion to releasably secure the removable lens to the face mask, and a release position, in which the catch is away from the connector portion, to enable removal of the removable lens from the face mask.

19. The protective mask according to claim 18, wherein the face mask defines channels on opposite sides of the opening, for receiving the connector portions of the removable lens, the channels each defining guide edges for guiding the connector portions into position with respect to the clamping devices.

20. The protective mask according to claim 19, wherein the connector portions and the channels are provided with corresponding abutments for aligning the connector portions into position with respect to the clamping devices.

* * * * *